United States Patent [19]
Chesterfield et al.

[11] Patent Number: 5,181,923
[45] Date of Patent: Jan. 26, 1993

[54] SPIROID BRAIDED SUTURE

[75] Inventors: Michael P. Chesterfield, Norwalk; Ilya Koyfman, Orange; Matthew E. Hain, New Haven, all of Conn.

[73] Assignee: United States Surgical Corporation, Norwalk, Conn.

[21] Appl. No.: 569,063

[22] Filed: Aug. 17, 1990

Related U.S. Application Data

[63] Continuation-in-part of Ser. No. 499,173, Mar. 26, 1990, Pat. No. 5,059,213.

[51] Int. Cl.⁵ ............................................. A61B 17/00
[52] U.S. Cl. .................................... 606/228; 606/230; 606/231
[58] Field of Search ................................. 606/228-231

[56] References Cited

U.S. PATENT DOCUMENTS 3,187,752  6/1965  Glick .
3,565,077  2/1971  Glick .
4,014,973  7/1973  Thompson .
4,043,344  8/1977  Landi et al. .
4,047,533  9/1977  Perciaccante et al. .
4,959,069  9/1990  Brennan et al. .
4,983,180  1/1991  Kawai et al. ......................... 606/230
5,019,093  5/1991  Kaplan et al. ......................... 606/228

OTHER PUBLICATIONS

Brown et al., "Acceleration of Tensile Strength of Incisions Treated with EFG and TGF-beta", *Ann. Surg.*, pp. 788 et seq. (Dec. 1988).

Barbul et al., eds., "Growth Factors and Other Aspects of Wound Healing/Biological and Clinical Implications", *Proceedings of the Second International Symposium on Tissue Repair*, Tarpon Springs, Fla., May 13–17, 1987 (Alan R. Liss, Inc., New York).

Lynch et al., "Growth Factors in Wound Healing", *J. Clin. Invest.*, vol. 84, Aug. 1989, pp. 640–646.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A suture is provided with a substantially solid spiroid braid construction. The suture exhibits greater flexibility, better hand and less chatter and drag than tubular braided sutures of known construction.

57 Claims, 4 Drawing Sheets

MAGNIFICATION=50X

MAGNIFICATION=150X

MAGNIFICATION=150X

MAGNIFICATION=200X

MAGNIFICATION=400X

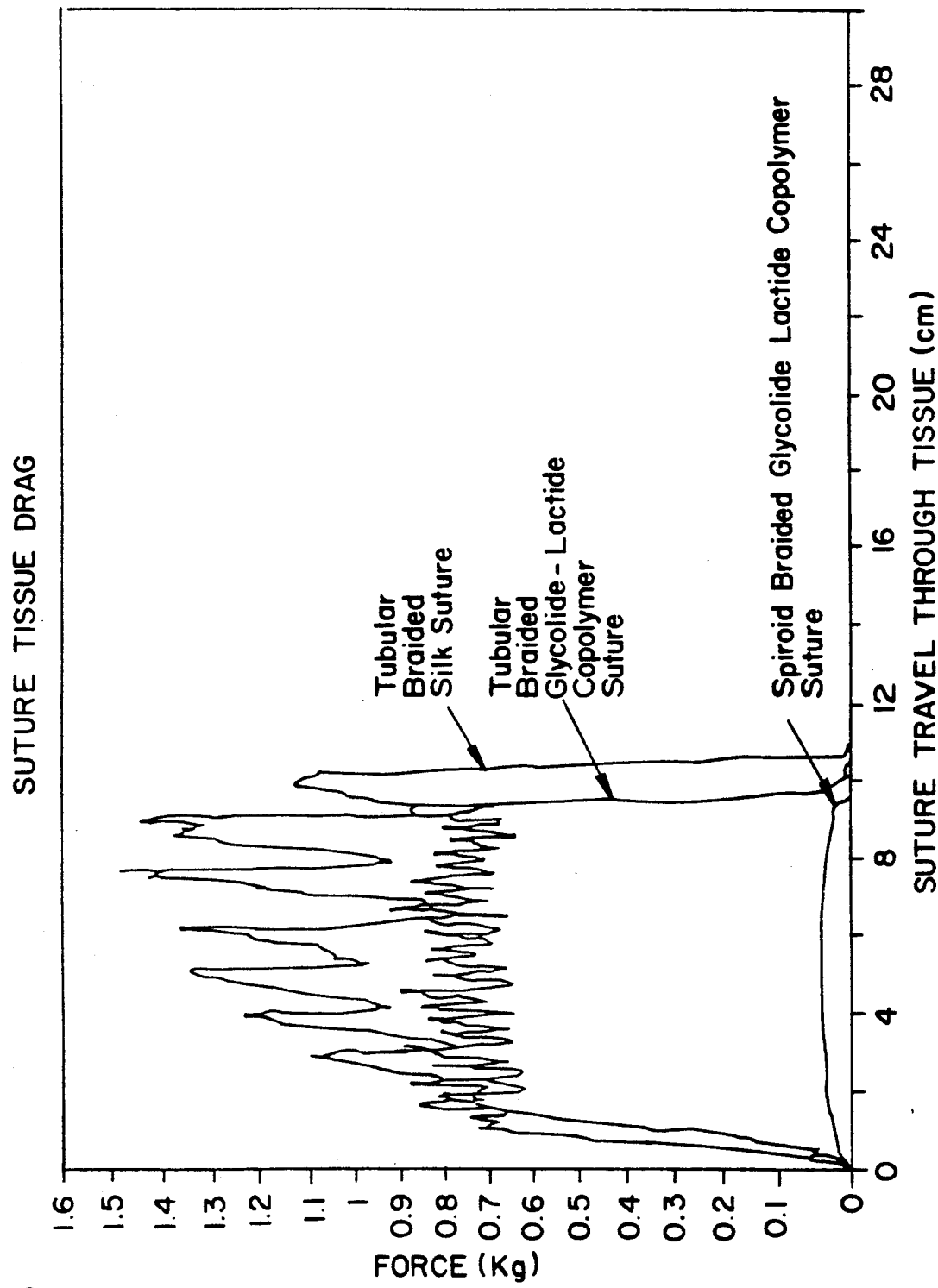

SPIROID BRAIDED SUTURE

CROSS REFERENCE TO RELATED APPLICATIONS

This application is a continuation-in-part of copending U.S. patent application Ser. No. 499,173, filed Mar. 26, 1990 now U.S. Pat. No. 5,059,213. This application also relates by subject matter to copending U.S. patent application Ser. No. 07/574,344 filed Aug. 21, 1990, U.S. patent application Ser. No. 07/570,345, filed Aug. 21, 1990, now U.S. Pat. No. 5,133,738, and copending U.S. patent application Ser. No. 07/658,681, filed Feb. 26, 1991 as a continuation-in-part of application Ser. No. 07/569,062, filed Aug. 17, 1990, now abandoned.

BACKGROUND OF THE INVENTION

This invention relates to a suture possessing a solid spiroid braid.

Sutures intended for the repair of body tissues must meet certain requirements: they must be substantially non-toxic, capable of being readily sterilized, they must have good tensile strength and have acceptable knot-tying and knot-holding characteristics and if the sutures are of the bio-absorbable variety, the bio-absorption of the suture must be closely controlled.

Sutures have been constructed from a wide variety of materials including surgical gut, silk, cotton, polyolefins such as polypropylene, polyamides, polyesters such as polyethylene terephthalate, polyglycolic acid, glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials have been provided as braided structures. Thus, for example, sutures manufactured from silk, polyamide, polyester and bio-absorbable glycolide-lactide copolymer are usually provided as multifilament braids.

Currently available braided suture products are braided on conventional braider-carriers which travel around the perimeter of the braider deck to result in a tubular type braid with the yarns crossing over each other on the surface of the braid. In the larger sizes, e.g., 5/0 and larger, the tubular braid, or sheath, is constructed about a core structure which is fed through the center of the braider. Known tubular braided sutures, including those possessing cores, are disclosed, e.g., in U.S. Pat. Nos. 3,187,752; 3,565,077; 4,014,973; 4,043,344; and, 4,047,533.

Spiroid braided structures per se are known, e.g., rope, sash cord and the like, but heretofore have not been known for use as sutures.

As removed from the package, the currently available tubular braided suture products exhibit one or more deficiencies. Thus, they tend to be stiff and wiry and retain a "set" or "memory" such that at the time of use, it is usually necessary for the surgeon or assistant personnel to flex and stretch the suture to make it more flexible. Furthermore, the surfaces of these sutures are perceptibly rough. Thus, if one passes one's hand or fingers along the braid, surface irregularities will be readily detected. The result of this rough surface is that the suture will exhibit drag or chatter as it is drawn through tissue, characteristics which militate against smooth, neat, accurately placed wound approximation so necessary to excellence in surgical practice.

SUMMARY OF THE INVENTION

It is an object of this invention to provide a braided suture of improved characteristics, specifically, one exhibiting greater flexibility, better hand and less chatter and drag, than braided sutures of known construction.

It is another object of the invention to provide a braided suture exhibiting improved knot security relative to known tubular braided suture constructions.

It is a particular object of the invention to improve the storage stability of a spiroid braided suture fabricated from an absorbable resin which is susceptible to hydrolysis, e.g., a suture based in whole or in part on a polyester homopolymer or copolymer such as polyglycolic acid, polyglycolide-lactide copolymer, etc., by filling the suture with a storage stabilizing agent or composition.

It is yet another object of the invention to apply one or more medico-surgically useful compositions to the spiroid braided suture to enhance or accelerate wound repair and/or tissue growth. A particularly advantageous composition of this type is one containing at least one Human Growth Factor (HGF), preferably in combination with a carrier such as glycerol which protects the HGF from excessive loss of biopotency during storage.

By way of satisfying the foregoing objects as well as other objects of the invention, there is provided in accordance with this invention a suture of spiroid braid construction.

Due to the substantially parallel orientation of the fibers relative to its axis, the spiroid braided suture of this invention exhibits improved flexibility and hand and reduced tissue chatter and drag compared with tubular and/or cored braided sutures where the fibers cross over each other.

Unlike tubular braided sutures, the spiroid braided suture of this invention shows little if any tendency to kink or snarl. Bends which might cause core popping (the penetration of the core through the braided sheath) in the known types of tubular braided sutures pose no risk of damage to the preferred spiroid braided suture of this invention.

Knot security in the spiroid braided suture of this invention is also superior to that obtainable with known tubular braided constructions. Factors contributing to enhanced knot security include the approximately perpendicular orientation of the fibers in the knot relative to the axis of the braid, the reduced density of the knot compared with the knot of a cored suture of equivalent size and the formation of a narrowed-down portion which makes the knot more difficult to untie.

The term "suture" as used herein is intended to embrace both the non-absorbable as well as the bio-absorbable varieties.

The expressions "spiroid braid" and "spiroid braided" as applied to the suture of this invention refer to a substantially solid arrangement of discrete units, or bundles, denominated "yarns", made up of individual filaments or fibers with the yarns arranged substantially parallel to the longitudinal axis of the suture and internally engaging each other in a repetitive spiral pattern.

The term "solid" as applied to the suture herein is intended to designate a suture in which the filamentous material of its construction occupies substantially the entire cross-sectional area of the suture with at most a minor percentage, not exceeding about 25% in the larger suture sizes, of such area constituting void space or interstices between adjacent yarns and fibers. Such a construction contrasts with that of a standard suture which, in the absence of a core component, possesses a lumen representing a significant percentage of the cross-sectional area of the suture.

The term "standard suture" is intended to designate any of the heretofore known braided sutures, e.g., those described in U.S. Pat. No. 3,565,077, the contents of which are incorporated by reference herein, and in particular, braided suture products marketed by Ethicon, Inc. under its Vicryl brand and those marketed by Davis & Geck, Inc. (American Cyanamid Company) under its Dexon brand.

DESCRIPTION OF THE PREFERRED EMBODIMENTS

Figure 1:
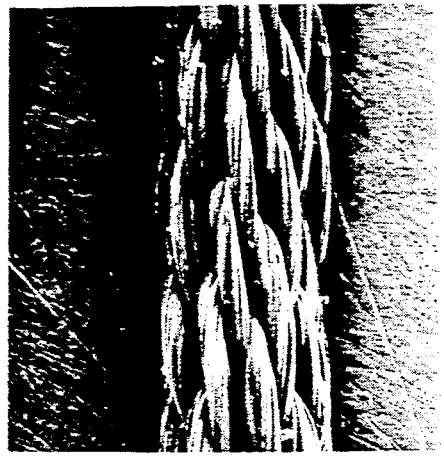
FIGS. 1-5 are photomicrographs of linear (FIGS. 1 and 2) and cross-sectional (FIGS. 3, 4 and 5) views taken by scanning electron microscopy (SEM) of a spiroid braided suture in accordance with the present invention.

The spiroid braided suture of this invention can be fabricated from a wide variety of natural and synthetic fibrous materials such as any of those heretofore disclosed for the construction of sutures. Such materials include non-absorbable as well as partially and fully bio-absorbable (i.e., resorbable) natural and synthetic fiber-forming polymers. Non-absorbable materials which are suitable for fabricating the spiroid braided suture of this invention include silk, polyamides, polyesters such as polyethylene terephthalate, polyacrylonitrile, polyethylene, polypropylene, silk, cotton, linen, etc. Carbon fibers, steel fibers and other biologically acceptable inorganic fibrous materials can also be employed. Bio-absorbable resins from which the spiroid suture can be fabricated include those derived from glycolic acid, glycolide, lactic acid, lactide, dioxanone, epsilon-caprolactone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,787,284; 3,982,543; 4,047,533; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459-1464 (1979), and D. F. Williams (ed.), *Biocompatibility of Clinical Implant Materials*, Vol. II, ch. 9: "Biodegradable Polymers" (1981).

The defining characteristics of a specific spiroid braided suture in accordance with this invention, apart from the material of its construction, are:

(1) suture size (i.e., suture diameter)
(2) overall suture denier;
(3) the pattern of the interlocking yarns;
(4) pick count;
(5) the number of yarns comprising the braid;
(6) the denier of the filaments comprising each yarn; and,
(7) the denier of the core, where present.

(1) Suture Size (i.e.. Suture Diameter)

The suture size can be expressed in terms of standard sizes, corresponding to certain ranges of diameter (in millimeters), as set forth in the *United States Pharmacopoeia* (USP). Standard sizes of the spiroid braided suture herein are set forth in Table I as follows:

TABLE I

| SUTURE SIZE | |
|---|---|
| USP Suture Size | Diameter (mm) |
| 2 | 0.50–0.599 |
| 1 | 0.40–0.499 |
| 0 (1/0) | 0.35–0.399 |
| 2/0 | 0.30–0.399 |
| 3/0 | 0.20–0.249 |
| 4/0 | 0.15–0.199 |
| 5/0 | 0.10–0.149 |
| 6/0 | 0.070–0.099 |
| 7/0 | 0.050–0.069 |
| 8/0 | 0.040–0.049 |

(2) Overall Denier of the Suture

The overall denier of the braided suture can vary from about 20 to about 4000. Within this range, the ranges of overall denier for particular sutures are: from about 50 to about 125 denier; from above about 200 to about 300 denier; from above about 300 to about 500 denier; from above about 500 to about 800 denier; from above about 800 to about denier; from above about 1500 to about 2000 denier; and, from above about 2000 to about 3600 denier.

(3) Pattern of the Interlocking Yarns

Unlike a tubular braided structure where the yarns form a crisscross pattern which may be thought of as confined to the surface of a hollow cylinder, the spiroid braided suture of this invention consists of a pattern of interlocking yarns which may be considered as extending from the surface of cylinder to its center thus providing a substantially solid structure as defined above.

Figure 2:
Figure 3:
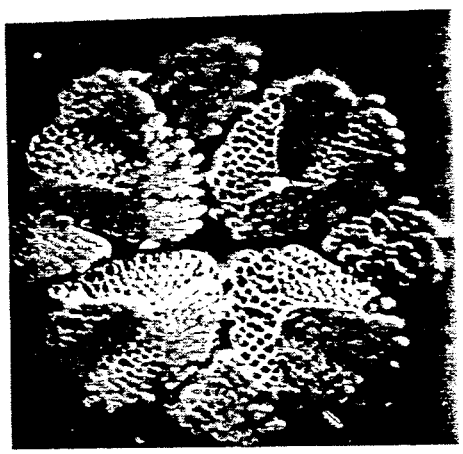
Figure 4:
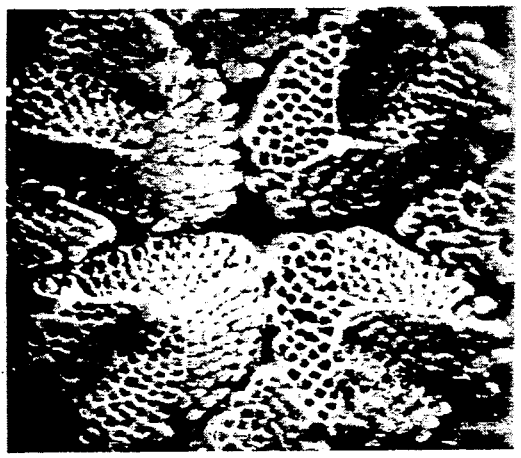
Figure 5:
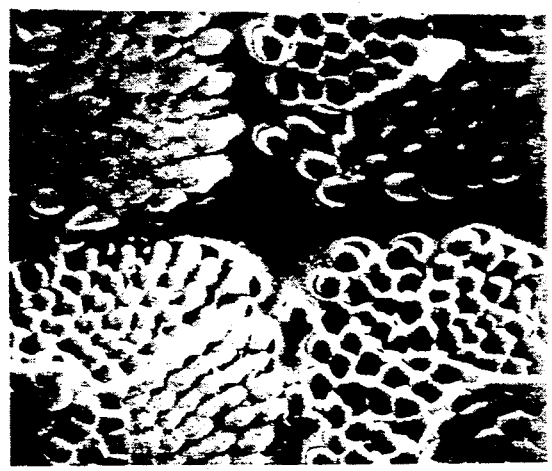
Figure 6:
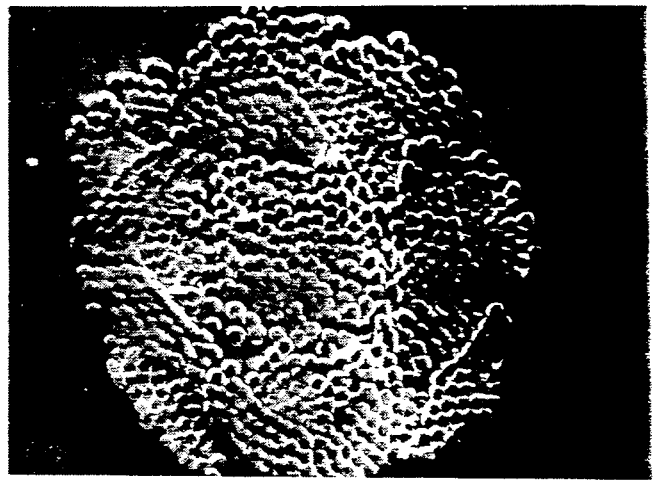
FIGS. 6 and 7 are photomicrographs of linear (FIG. 6) and cross-sectional (FIG. 7) views taken by SEM of a commercially available tubular braided suture possessing a core component; and, FIG. 8 is a graphical representation of the tissue drag of a spiroid braided suture compared with that of two types of commercially available tubular braided sutures.
Figure 7:

The characteristic pattern of a spiroid braided suture is clearly different from that of a tubular braided suture. In the former, the yarns are essentially parallel to the longitudinal axis of the suture whereas in the latter, the yarns cross over each other at some angle to the longitudinal axis of the suture. The structural differences between a spiroid braided suture of this invention and a tubular braided suture are clearly evident from a comparison of the linear and cross-sectional views of a spiroid braided suture (FIGS. 2 and 3) and a tubular braided suture (FIGS. 6 and 7).

(4) Pick Count

Pick count is the number of stitches per inch lying in a single line parallel to the longitudinal axis of the suture as viewed from the surface of the suture. Suitable pick counts can vary from about 10 to about 80 stitches/inch and preferably from about 20 to about 60 stitches/inch.

(5) The Number of Yarns

The number of yarns employed in the construction of the suture bears some relation to overall suture denier, the number of yarns generally increasing with the weight of the suture. Thus, across the range of suture weight (denier) indicated above, the spiroid braided suture of this invention can be fabricated with from about 6 up to as many as about 30 individual yarns constructed from individual filaments having the deniers discussed below.

Table II below sets forth broad and preferred ranges for the numbers of yarns which are suitable for the construction of spiroid braided sutures of various ranges of overall denier. The deniers of individual filaments in a yarn can vary from about 0.2 to about 6.0 for the broad range of number of yarns and the deniers of individual filaments can vary from about 0.8 to about 3.0, and advantageously from about 1.2 to about 2.5, for the preferred range of number of yarns.

TABLE II
NUMBER OF YARNS RELATED TO SUTURE DENIER

| Overall Suture Denier | Suture Size | Number of Yarns (Broad Range) | Number of Yarns (Preferred Range) |
|---|---|---|---|
| 50 to about 125 | 7/0, 8/0 | 3–12 | 3–6 |
| greater than about 125 to about 200 | 6/0 | 6–15 | 6–12 |
| greater than about 200 to about 300 | 5/0 | 6–15 | 6–12 |
| greater than about 300 to about 500 | 4/0 | 6–15 | 9–12 |
| greater than about 500 to about 800 | 3/0 | 9–20 | 12–15 |
| greater than about 800 to about 1200 | 2/0 | 12–25 | 15–20 |
| greater than about 1200 to about 2000 | 0 | 12–25 | 15–20 |
| greater than about 2000 to about 4000 | 1, 2 | 15–25 | 20–25 |

While the yarns need not be twisted, it is generally preferred that they be provided with a slight twist so as to minimize snagging during braid construction.

(6) Individual Filament Denier

The individual filaments comprising each yarn can vary from about 0.2 to about 6.0 denier, preferably from about 1.2 to about 2.5 denier and more preferably from about 0.8 to about 1.4 denier. The number of such filaments present in a particular yarn will depend on the overall denier of the suture as well as the number of yarns utilized in the construction of the suture. Table III sets forth some typical numbers of filaments per yarn for both the broad and preferred ranges of filament weight:

TABLE III
NUMBER OF FILAMENTS PER YARN

| approximate minimum | approximate maximum | Filament Denier |
|---|---|---|
| 45 | 1500 | 0.2 |
| 15 | 500 | 0.5 |
| 5 | 200 | 1.5 |
| 3 | 150 | 1.8 |
| 1 | 50 | 6.0 |

(7) Core (Optional)

For all but the smallest sizes of spiroid braided suture, the suture, although substantially solid in the sense defined above, can optionally contain some small amount of void space, generally not exceeding 25% or so in the larger suture sizes, which, if desired, can be partially or substantially completely filled with a core component. A core may be advantageous where it is desired to increase the density of the suture and/or preserve its roundness. The core, where present, can be monofilamentous or multifilamentous. In the case of the latter, the core itself can be braided or can be provided with some other configuration such as a twist, ply, cable, etc. The filament(s) comprising the core can be fabricated from a material which is the same as, or is different from, that of the braid. The core filament(s) can also possess a denier which is the same as, or is different from, that of the braid filaments.

Table IV below provides some typical core deniers for sutures of various deniers:

TABLE IV
CORE DENIER RELATED TO SUTURE DENIER

| Overall Suture Denier | Suture Size | Maximum Denier of Optional Core (Broad Range) | Maximum Denier of Optional Core (Preferred Range) |
|---|---|---|---|
| from about 50 to about 125 | 8/0, 7/0 | none | none |
| greater than about 125 to about 200 | 6/0 | 25–40 | 10–20 |
| greater than about 200 to about 300 | 5/0 | 40–60 | 20–30 |
| greater than about 300 to about 500 | 4/0 | 60–100 | 30–50 |
| greater than about 500 to about 800 | 3/0 | 125–200 | 75–120 |
| greater than about 800 to about 1200 | 2/0 | 200–300 | 120–180 |
| greater than about 1200 to about 2000 | 0 | 300–500 | 180–300 |
| greater than about 2000 to about 4000 | 1, 2 | 500–1000 | 300–600 |

It is to be understood that Table IV merely sets forth suitable maximum core deniers where a core is present. The actual core denier for a given suture can be substantially less than the indicated maximum.

When the spiroid braided suture of this invention is fabricated from a material which is susceptible to hydrolysis, e.g., any of the absorbable resins previously mentioned, care must be taken to rigorously exclude moisture from contacting the suture during storage or to otherwise preserve the suture from excessive hydrolytic attack which would compromise its in vivo strength to the point where the suture would no longer be serviceable.

According to U.S. Pat. Nos. 3,728,839 and 4,135,622, the in vivo strength of polyglycolic acid surgical elements such as sutures undergoes significant deterioration on long term standing in the package even on exposure of the contents to very small amounts of water for very short periods of time, e.g., 20 minutes or less, just prior to packaging due to the tendency of a moisture impervious package to seal the moisture in with the suture. To prevent or minimize the extent of hydrolytic degradation of an absorbable suture during storage expressed, for example, as a reduction in out-of-package tensile strength, U.S. Pat. Nos. 3,728,839 and 4,135,622 disclose removing moisture from the suture before sealing the package so that no more than about 0.5 percent of water by weight of suture remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°-188° C. for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore become necessary following the water removal step to temporarily store the suture in a dry area, i.e., an environment which is essentially free of moisture, where the possibility of contact with moisture is largely eliminated. These operations for improving the storage stability of an absorbable suture are time consuming, expensive and constitute a relatively complex solution to the storage stability problem.

In an entirely different approach to improving the storage stability of an absorbable suture, one that avoids the foregoing drawbacks associated with the method of U.S. Pat. Nos. 3,728,839 and 4,135,622, the storage stability of an absorbable spiroid braided suture which is susceptible to hydrolysis is improved by applying to the suture a storage stabilizing amount of at least one water soluble liquid polyhydroxy compound and/or ester thereof. In addition to imparting an enhanced degree of storage stability to the suture, practice of this embodiment of the present invention confers other benefits as well. So, for example, a spiroid braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances, they can be used as vehicles to deliver such substances to a wound or surgical site at the time the suture is introduced into the body.

The useful storage stabilizing agents are generally selected from the water soluble, liquid polyhydroxy compounds and/or esters of such compounds, preferably those having no appreciable toxicity for the body at the levels present. The expression "liquid polyhydroxy compound" contemplates those polyhydroxy compounds which in the essentially pure state are liquids, as opposed to solids, at or about ambient temperature, e.g., at from about 15° C. to about 40° C. The preferred polyhydroxy compounds possess up to about 12 carbon atoms and where the esters are concerned, are preferably the monoesters and diesters. Among the specific storage stabilizing agents which can be used with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of storage stabilizing agents, e.g., sorbitol dissolve din glycerol, glycerol combined with monoacetin and/or diacetin, etc., are also useful.

To prevent or minimize run-off or separation of the storage stabilizing agent from the suture, a tendency to which relatively low viscosity compounds such as glycerol are especially prone, it can be advantageous to combine the agent with a non-aqueous thickener. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015 referred to above, polysaccharide gums such as guar, xanthan, and the like, gelatin, collagen, etc. An especially preferred class of thickeners are the saturated aliphatic hydroxycarboxylic acids of up to 6 carbon atoms and the alkali metal and alkaline earth metal salts and hydrates thereof. Within this preferred class of compounds are those corresponding to the general formula

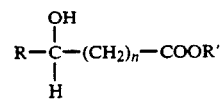

wherein R is hydrogen or methyl, R' is a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinbefore, hydrates of these compounds can also be used. Calcium lactate, especially calcium lactate pentahydrate, is a particularly preferred thickener.

Where a thickener is utilized, it will be incorporated in the filling composition in at least that amount required to increase the overall viscosity of the composition to the point where the composition no longer readily drains away from the suture in a relatively short period. In the case of a preferred carrier-thickener combination, namely, glycerol and calcium lactate, the weight ratio of glycerol to calcium lactate can vary from about 1:1 to about 10:1 and preferably is from about 6:1 to about 8:1.

If necessary or desirable, the stabilizing agent together with optional thickener can be dissolved in any suitable non-aqueous solvent or combination of solvents prior to use. To be suitable, the solvent must (1) be miscible with the storage stabilizing agent and optional thickener, (2) have a sufficiently high vapor pressure to be readily removed by evaporation, (3) not appreciably affect the integrity of the suture and (4) be capable of wetting the surface of the suture. Applying these criteria to a preferred storage stabilizing agent, glycerol, advantageously in admixture with a preferred thickener, calcium lactate, lower alcohols such as methanol and ethanol are entirely suitable solvent carriers. When a solvent is utilized in the preparation of the stabilizing agent, such solvent, e.g., methanol, can be employed in an amount providing a solution concentration of from about 20% to about 50%, preferably about 30% to about 45%, by weight of the storage stabilizing agent including any optional thickener based on the total weight of the solution.

Preparing the storage stabilizing agent for application to the suture is a relatively simple procedure. For example, in the case of a mixture of glycerol and calcium lactate, the desired amount of glycerol is first introduced to a suitable vessel followed by the addition thereto of the desired amount of calcium lactate. If no solvent is to be used, the mixture is then thoroughly mixed. Where a solvent such as methanol is employed, the solvent is added to the mixture of glycerol and calcium lactate and the solution is then thoroughly mixed to dissolve the compounds.

Application of the storage stabilizing agent to the suture can be carried out in any number of ways. Thus, for example, the suture can be submerged in the storage stabilizing agent or solution thereof until at least a storage stabilizing amount of agent is acquired or otherwise retained by the suture, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 20 hours and even longer, are sufficient to impart a substantial improvement in the storage stability of the treated suture compared to the same suture which has not been treated with storage stabilizing agent. It has been found that calendering the suture prior to filling, such as by passing the suture through at least two transversely mounted pairs of calendar rolls, improves receptivity of the suture to filling and improves the suppleness of the resulting filled suture. It is believed that calendering the suture separates the individual suture filaments to open up spaces therebetween which are conducive to ensuring that the filling composition penetrates within, and fills, the interstices of the spiroid braided suture.

The foregoing submersion method of contacting the suture with storage stabilizing agent can be conducted continuously or in batch. Thus, a running length of the suture can be continuously passed through a quantity of the stabilizing agent at a velocity which has been previously determined to provide the necessary degree of exposure, or contact time, of the suture with the storage stabilizing agent As the suture emerges from the storage stabilizing agent, it can be passed through a wiper or similar device to remove excess agent prior to the packaging operation. Preferably, the suture is passed through a coating head supplied by a metering pump with a constant supply of filling solution, with the suture emerging from the coating head and passing through an evaporation oven to remove the filling solution solvent prior to any further surface contact, i.e., with rollers, etc. In a batch operation, a quantity of suture is merely submerged within the storage stabilizing agent for the requisite period of time with any excess agent being removed from the suture if desired.

Alternatively, the storage stabilizing agent and solutions thereof can be applied to the suture by spraying, brushing, wiping, etc., such that the suture receives and retains at least a storage stabilizing amount of the agent Yet another procedure which can be used to apply the storage stabilizing agent involves inserting the suture in a package containing an effective amount of the agent such that intimate contact between the suture and the agent is achieved.

Whatever the contacting procedure employed, it is necessary that the suture being treated acquire a storage stabilizing amount of the storage stabilizing agent. In general amounts of from about 2 to about 25, and preferably from about 5 to about 15 weight percent, of storage stabilizing agent(s) (exclusive of any solvent) by weight of the suture contacted therewith is sufficient to provide significantly improved storage stabilizing compared to that of the untreated suture.

As previously pointed out, a filled spiroid braided suture in accordance with the invention need not be packaged and maintained under the very dry conditions required for prior synthetic absorbable sutures. Instead, it is preferred that the filled sutures be equilibrated so that the level of moisture or other stabilizing agent solvent is sufficient to result in an appropriate viscosity level for the stabilizing agent and thickener in order to keep the stabilizing agent on the suture. In the preferred embodiment of a spiroid braided suture filled with a mixture of glycerol and calcium lactate, the moisture level may be equilibrated to as low as about 0.2% by weight of the suture, and is preferably above 0.3% or, even more preferably, above 0.5% by weight of the suture.

Indeed, it has been found that a spiroid braided suture filled with glycerol/calcium lactate composition tends to undergo undesirable changes if exposed to a very dry environment. More particularly, if such a filled suture is exposed to a very dry environment, the surface of the suture may accumulate a flaked or powdered substance which could possibly interfere with, or render more difficult, the removal of the suture from its package. Equilibrating the filled suture, such as in a dew point controlled environment, so that the suture contains a relatively high moisture level, e.g., in excess of 0.2% and preferably in excess of 0.5% by weight of the suture, prevents such accumulation of flaked or powdered substance which might otherwise result were the suture exposed to an extremely dry environment. Conversely, the presence of too much moisture can also have deleterious effects, such as causing the glycerol filling to run. Therefore, it is preferable to control the moisture level within a range having preset upper and lower limits.

It is also within the scope of this invention to impregnate the spiroid braided suture of this invention with, or otherwise apply thereto, one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the spiroid braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mutagenically active and as such are effective in stimulating, accelerating, potentiating or otherwise enhancing the wound healing process can be usefully applied to the suture herein, e.g., hEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497, 3,917,824, 3,948,875, 4,338,397, 4,418,691, 4,528,186, 4,621,052, 4,743,679, 4,717,717, 4,861,757, 4,874,746 and 4,944,948, European Patent Applications Nos. 46,039, 128,733, 131,868, 136,490, 147,178, 150,572, 177,915 and 267,015, PCT International Applications WO 83/04030, WO 85/003698, WO 85/01284 and WO 86/02271, UK Patent Applications GB 2 092 155 A, 2 162 851 A and GB 2 172 890 A and, "Growth Factors in Wound Healing", Lynch, et al., *J. Clin. Invest.*, Vol. 84, pages 640–646 (August 1989) all of which are incorporated by reference herein. Of the known HGFs, hEGF, TGF-beta, IGF, PDGF and FGF are preferred, either singly or in combination.

In a preferred embodiment of the spiroid braided suture of this invention, a filling composition comprising a surgical wound healing enhancing amount of at least one HGF and as carrier therefor at least one water soluble, liquid polyhydroxy compound and/or ester thereof such as any of those previously mentioned is applied to the suture. The carrier, e.g., glycerol which is especially preferred, protects the HGF component of the filling composition from excessive degradation or loss of biopotency during storage and, as disclosed above, when the suture is fabricated from an absorbable resin which is susceptible to hydrolysis, the carrier improves the storage stability of the suture as well. In addition to carrier, the HGF can contain a thickener such as any of those previously mentioned in order to reduce the tendency of carrier run-off.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See, e.g., Tomlinson (Ciba-Geigy Pharmaceuticals, West Sussex, U.K.), "Selective Delivery and Targeting of Therapeutic Proteins", a paper presented at a symposium held June 12-14, 1989 in Boston, MA, the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of Bio-Growth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

The amounts of HGF, carrier and optional component(s) such as thickener, site-specific hybrid protein, carrier protein, etc., identified above can vary widely and in general will be at least that amount of a particular component which is required to perform its respective function in an effective way. Those skilled in the art employing known or conventional procedures can readily determine optimum amounts of each component for a particular filling composition and particular spiroid braided suture filled therewith.

In general, the HGF(s) can be present in the total composition at a level ranging from about 0.1 to about 25,000 micrograms per gram of such composition, preferably from about 0.5 to about 10000 micrograms per gram of composition and most preferably from about 1 to about 50–0 micrograms per gram of composition.

Application of the HGF-containing composition to the spiroid braided suture of this invention can be carried out by any suitable technique, e.g., by any of the procedures described above for applying a storage stabilizing agent to the suture.

It can also be advantageous to apply one or more coating compositions to the spiroid braided suture where particular functional properties are desired. For example, the suture can be coated with a material which improves its surface lubricity and/or knot tie-down characteristics. Suitable materials which impart either or both characteristics include the bioabsorbable coating compositions obtained by copolymerizing in accordance with known procedures (1) a polyether glycol selected from the group consisting of relatively low molecular weight polyalkylene glycol, e.g., one corresponding to the general formula $HO(RO)_yH$ wherein R is an alkylene group of from 2–4 carbon atoms and y is an integer of from about 100–350, and polyethylene oxide-polypropylene oxide block copolymer, e.g., one corresponding to the general formula $H(OCH_2CH_2)_x(OC_3H_6)_y(OCH_2CH_2)_zOH$ wherein x is an integer of from about 45–90, y is an integer of from about 60–85 and z is an integer of from about 45–90, y is an integer of from about 60–85 and z is an integer of from about 45–90 with (2) a mixture of lactide monomer and glycolide monomer or a preformed copolymer of lactide and glycolide, the weight ratio of (1) to (2) preferably ranging from about 4:1 to about 1:4 and more preferably from about 2:1 to about 1:2. The ratio of lactide to glycolide in the monomer mixture or in the copolymer of these monomers preferably varies from about 65–90 mole percent lactide and 10–35 mole percent glycolide. Polyether glycols which can be used to prepare the bioabsorbable coating composition advantageously include polyethylene glycols which can be used to prepare the bioabsorbable coating composition advantageously include polyethylene glycols having molecular weights of about 1 3,500–25,000 and preferably from about 4,000–10,000 and polyethylene oxide-polypropylene oxide block copolymers having molecular weights of from about 5,000–10,000 and preferably from about 7,500 to about 9,000, e.g., those disclosed in U.S. Pat. Nos. 2,674,619, 3,036,118, 4,043,344 and 4,047,533 and commercially available as the Pluronics (BASF-Wyandotte). Where preformed copolymers of lactide and glycolide are employed in preparing the bioabsorbable coating compositions, they may be prepared as described in U.S. Pat. No. 4,523,591. The amounts of bioabsorbable coating composition to be applied to the suture, e.g., by coating, dipping, spraying or other appropriate technique, will vary depending upon the specific construction of the suture, its size and the material of its construction. In general, the coating composition applied to an unfilled suture will constitute from about 1.0 to about 3.0 percent by weight of the coated suture, but the amount of coating add on may range from as little as about 0.5 percent, by weight, to as much as 4.0 percent or higher. For a preferred filled (i.e., containing a storage stabilizing agent) braided suture, amounts of coating composition will generally vary from about 0.5% to 2.0% with as little as 0.2% to as much as 3.0%. As a practical matter and for reasons of economy and general performance, it is generally preferred to apply the minimum amount of coating composition consistent with good surface lubricity and/or knot tie-down characteristics and this level of coating add on is readily determined experimentally for any particular suture.

The following examples are illustrative of the spiroid braided suture of this invention.

EXAMPLE 1

A size 2/0 spiroid braided suture was constructed from 90/10 weight percent glycolide-lactide copolymer filaments in accordance with the invention. The suture had an overall denier of about 1300. The suture was made from a total of 20 yarns with each filament having a denier of 1.2. The scanning electron photomicrographs of FIGS. 1-5 show the 2/0 spiroid braided suture at various levels of magnification. The substantially parallel orientation of the individual yarns and fibers relative to the longitudinal axis of the suture is clearly evident from FIGS. 1 and 2 at magnifications of 50x and 150x, respectively. The cross-sectional views of the suture shown in FIGS. 3, 4 and 5 at magnifications of 150x, 200x and 400x, respectively, show the substantially solid nature of the suture, there being relatively little unfilled space between adjacent yarns.

FIGS. 6 and 7, photomicrographs of linear and cross-sectional views, respectively, taken by SEM of a commercially available tubular braided suture possessing a core component, are presented by way of comparison with the solid, tubular braided sutures shown in FIGS. 1-5. The distinctly different structures of the two types of suture construction are clearly evident and can be readily appreciated.

As a result of its unique construction characteristics, the spiroid braided suture of this invention exhibits significantly improved flexibility and hand and reduced chatter and drag compared with known sutures. For a given size spiroid suture, it is possible to reduce tissue drag to a substantial degree compared with the tissue drag exhibited by a standard braided suture, particularly in the case of standard braided sutures now on the market. In such cases, the spiroid braided suture of this invention will often be less than 60%, preferably less than 40% and still more preferably less than 20%, of the level of tissue drag exhibited by standard braided suture products of comparable size (denier).

EXAMPLE 2

This example compares three size 2/0 sutures for tissue drag. Two of the sutures, a surface-coated tubular braided silk suture and a surface-coated tubular braided glycolide-lactide copolymer suture, are commercially available. The third, a surface-coated and filled solid spiroid braided glycolide-lactide copolymer suture, is representative of the suture of this invention.

The tissue drag profiles of the three sutures appear in FIG. 8 as the plot of force (kg) required to pull each suture through animal facial tissue through a distance of somewhat greater than 10 cm. As the graphically represented data show, the braided suture constructed in accordance with the criteria of this invention exhibits a dramatically reduced level of tissue drag compared with that of the other two braided sutures.

EXAMPLES 3-11

These examples illustrate various size spiroid braided sutures which can be fabricated from bioabsorbable materials, e.g., the 90/10 weight percent glycolide-lactide copolymer employed in the fabrication of the suture of Example 1.

| Example | Size | Overall Suture Denier | Number of Yarns | Denier of Individual Filaments |
| --- | --- | --- | --- | --- |
| 3 | 7/0 | 50 | 6 | 1.6 |
| 4 | 6/0 | 120 | 9 | 1.6 |
| 5 | 5/0 | 320 | 12 | 1.6 |
| 6 | 4/0 | 430 | 12 | 1.6 |
| 7 | 3/0 | 700 | 15 | 1.6 |
| 8 | 2/0 | 1300 | 20 | 1.6 |
| 9 | 0 | 1500 | 20 | 1.6 |
| 10 | 1 | 2250 | 25 | 1.6 |
| 11 | 2 | 2960 | 25 | 1.6 |

EXAMPLES 12-20

These examples illustrate various size spiroid braided sutures which can be fabricated from nylon filaments.

| Example | Size | Overall Suture Denier | Number of Yarns | Denier of Individual Filaments |
| --- | --- | --- | --- | --- |
| 13 | 7/0 | 50 | 4 | 1.6-2.5 |
| 14 | 6/0 | 65 | 9 | 1.6-2.5 |
| 15 | 5/0 | 175 | 12 | 1.6-2.5 |
| 16 | 4/0 | 300 | 12 | 1.6-2.5 |
| 17 | 3/0 | 400 | 15 | 1.6-2.5 |
| 18 | 2/0 | 760 | 20 | 1.6-2.5 |
| 19 | 0 | 1100 | 20 | 1.6-2.5 |
| 20 | 1 | 1700 | 25 | 1.6-2.5 |
| 21 | 2 | 2230 | 25 | 1.6-2.5 |

EXAMPLES 21-29

These examples illustrate various size spiroid braided sutures which can be fabricated from nonabsorbable polyester, e.g., the polyethylene terephthalate resin Dacron (DuPont).

| Example | Size | Overall Suture Denier | Number of Yarns | Denier of Individual Filaments |
| --- | --- | --- | --- | --- |
| 21 | 7/0 | 60 | 4 | 1.6-2.5 |
| 22 | 6/0 | 100 | 9 | 1.6-2.5 |
| 23 | 5/0 | 220 | 12 | 1.6-2.5 |
| 24 | 4/0 | 360 | 12 | 1.6-2.5 |
| 25 | 3/0 | 510 | 15 | 1.6-2.5 |
| 26 | 2/0 | 960 | 20 | 1.6-2.5 |
| 27 | 0 | 1320 | 20 | 1.6-2.5 |
| 28 | 1 | 1930 | 25 | 1.6-2.5 |
| 29 | 2 | 2700 | 25 | 1.6-2.5 |

EXAMPLE 30

This example is illustrative of a size 2/0 spiroid braided glycolide-lactide copolymer suture filled with a wound healing enhancing amount of an HGF- and carrier/storage stabilizing agent-containing filling composition.

A solution of glycerol (278 gm), calcium lactate (43 gm) and sterile water (370 gm) is prepared. Human Growth Factor hEGF-51 (152.6 mg) (Creative Biomolecules, Inc., Hopkinton, MA) is dissolved volumetrically to 25 mL with the above solution to provide a braided suture filling composition. The composition is placed in the syringe pump of a suture coating apparatus. The syringe pump is set to provide the filling composition at a constant rate and the suture speed is adjusted to apply 17ml of filling composition to 200 meters of braid. The target concentration of HGF on the braid is 0.52 mg hEGF/meter or approximately 1.8 mg hEFG/gram of braid. After filling, the braid is immediately passed through a 50° drying column. After filling, the spooled braid is removed to a small chamber and stored under a flowing dry nitrogen atmosphere to remove the water from the solution.

While the foregoing description contains many specifics, these specifics should not be construed as limitations on the scope of the invention, but merely as exemplifications of preferred embodiment thereof. Those skilled in the art will envision many other possible variations that are within the scope and spirit of the invention as defined by the accompanying claims.

What is claimed is:

1. A suture of solid spiroid braid construction coated with a composition which results in a reduced level of tissue drag for the suture compared with the tissue drag of a standard suture of the same overall denier, said suture being fabricated from a material which is susceptible to hydrolysis, the suture possessing a storage stabilizing amount of at least one water soluble, liquid polyhydroxy compound and/or ester thereof as storage stabilizing agent.

2. The suture of claim 1 exhibiting a level of tissue drag which does not exceed about 60% of the level of tissue drag of a standard suture of the same overall denier.

3. The suture of claim 1 exhibiting a level of tissue drag which does not exceed about 40% of the level of tissue drag of a standard suture of the same overall denier.

4. The suture of claim 1 exhibiting a level of tissue drag which does not exceed about 20% of the level of tissue drag of a standard suture of the same overall denier.

5. The suture of claim 1 wherein for a given overall suture denier, the number of yarns and denier of individual filaments comprising a yarn of the spiroid braided suture are related to each other as follows:

| Overall Suture Denier | Number of Yarns | Denier of Individual Filaments |
| --- | --- | --- |
| from about 50 to about 125 | from about 6 to about 15 | from about 0.2 to about 6.0 |
| greater than about 125 to about 200 | from about 6 to about 15 | from about 0.2 to about 6.0 |
| greater than about 200 to about 300 | from about 6 to about 15 | from about 0.2 to about 6.0 |
| greater than about 300 to about 500 | from about 6 to about 15 | from about 0.2 to about 6.0 |
| greater than about 500 to about 800 | from about 9 to about 20 | from about 0.2 to about 6.0 |
| greater than about 800 to about 1200 | from about 12 to about 25 | from about 0.2 to about 6.0 |
| greater than about 1200 to about 2000 | from about 12 to about 25 | from about 0.2 to about 6.0 |
| greater than about 2000 to about 4000 | from about 15 to about 25 | from about 0.2 to about 6.0. |

6. The suture of claim 1 wherein for a given overall suture denier, the number of yarns and denier of individual filaments comprising a yarn of the spiroid braided suture are related to each other as follows:

| Overall Suture Denier | Number of Yarns | Denier of Individual Filaments |
| --- | --- | --- |
| from about 50 to about 125 | from about 6 to about 12 | from about 0.8 to about 3.0 |
| greater than about 125 to about 200 | from about 6 to about 12 | from about 0.8 to about 3.0 |
| greater than about 200 to about 300 | from about 6 to about 12 | from about 0.8 to about 3.0 |
| greater than about 300 to about 500 | from about 9 to about 12 | from about 0.8 to about 3.0 |
| greater than about 500 to about 800 | from about 12 to about 15 | from about 0.8 to about 3.0 |
| greater than about 800 to about 1200 | from about 15 to about 20 | from about 0.8 to about 3.0 |
| greater than about 1200 to about 2000 | from about 15 to about 20 | from about 0.8 to about 3.0 |
| greater than about 2000 to about 4000 | from about 24 to about 34 | from about 0.8 to about 3.0. |

7. The suture of claim 1 possessing a core.

8. The suture of claim 1 possessing a core, the maximum denier of the core for a given overall suture denier being as follows:

| Overall Suture Denier | Maximum Denier of Core |
| --- | --- |
| greater than about 125 to about 200 | 25–40 |
| greater than about 200 to about 300 | 40–60 |
| greater than about 300 to about 500 | 60–100 |
| greater than about 500 to about 800 | 125–200 |
| greater than about 800 to about 1200 | 200–300 |
| greater than about 1200 to about 2000 | 300–500 |
| greater than about 2000 to about 4000 | 500–1000. |

9. The suture of claim 1 possessing a core, the maximum denier of the core for a given overall suture denier being as follows:

| Overall Suture Denier | Maximum Denier of Core |
|---|---|
| greater than about 125 to about 200 | 10-20 |
| greater than about 200 to about 300 | 20-30 |
| greater than about 300 to about 500 | 30-50 |
| greater than about 500 to about 800 | 75-120 |
| greater than about 800 to about 1200 | 120-180 |
| greater than about 1200 to about 2000 | 180-300 |
| greater than about 2000 to about 4000 | 300-600. |

10. The suture of claim 1 wherein the individual filaments are fabricated from a bio-absorbable polymer.

11. The suture of claim 10 wherein the individual filaments are fabricated from a polymer derived at least in part from one or more monomers selected from the group consisting of glycolic acid, glycolide, lactic acid and lactide.

12. The suture of claim 1 wherein the water soluble, liquid polyhydroxy compound is glycerol.

13. The suture of claim 12 wherein the glycerol is admixed with calcium lactate.

14. The suture of claim 1 wherein the water soluble, liquid polyhydroxy compound is admixed with a nonaqueous thickener.

15. The suture of claim 1 wherein the water soluble, liquid polyhydroxy compound is admixed with a saturated aliphatic hydroxycarboxylic acid of the general formula

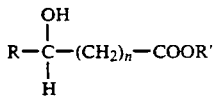

wherein R is hydrogen or methyl, R' is a metal selected from the group consisting of alkali metal and alkaline earth metal and n is 0 or 1 and hydrates thereof.

16. The suture of claim 15 wherein the water soluble, liquid polyhydroxy compound is admixed with calcium lactate.

17. The suture of claim 1 wherein the composition is a bioabsorbable coating composition obtained by copolymerizing a polyether glycol with a mixture of lactide monomer and glycolide monomer or a preformed copolymer of lactide and glycolide.

18. The suture of claim 17 wherein the polyether glycol is selected from the group consisting of low molecular weight polyalkylene glycol and polyethylene oxidepolypropylene oxide copolymer.

19. The suture of claim 17 wherein the water soluble, liquid polyhydroxy compound is glycerol.

20. The suture of claim 17 wherein the water soluble, liquid polyhydroxy compound is admixed with a nonaqueous thickener.

21. The suture of claim 17 wherein the water soluble, liquid polyhydroxy compound is admixed with a saturated aliphatic hydroxycarboxylic acid of the general formula

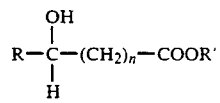

wherein R is hydrogen or methyl, R' is a metal selected from the group consisting of alkali metal an alkaline earth metal and n is 0 or 1 and hydrates thereof.

22. The suture of claim 21 wherein the water soluble, liquid polyhydroxy compound is admixed with calcium lactate.

23. The suture of claim 19 wherein the glycerol is admixed with calcium lactate.

24. The suture of claim 1 containing at least one medico-surgically useful substance.

25. The suture of claim 1 wherein the medico-surgically usefully useful substance is a Human Growth Factor.

26. The suture of claim 7 wherein for a given overall suture denier, the number of yarns and denier of individual filaments comprising a yarn of the spiroid braided suture are related to each other as follows:

| Overall Suture Denier | Number of Yarns | Denier of Individual Filaments |
|---|---|---|
| from about 50 to about 125 | from about 6 to about 15 | from about 0.2 to about 6.0 |
| greater than about 125 to about 200 | from about 6 to about 15 | from about 0.2 to about 6.0 |
| greater than about 200 to about 300 | from about 6 to about 15 | from about 0.2 to about 6.0 |
| greater than about 300 to about 500 | from about 6 to about 15 | from about 0.2 to about 6.0 |
| greater than about 500 to about 800 | from about 9 to about 20 | from about 0.2 to about 6.0 |
| greater than about 800 to about 1200 | from about 12 to about 25 | from about 0.2 to about 6.0 |
| greater than about 1200 to about 2000 | from about 12 to about 25 | from about 0.2 to about 6.0 |
| greater than about 2000 to about 4000 | from about 15 to about 25 | from about 0.2 to about 6.0. |

27. The suture of claim 26 wherein the maximum denier of the pore for a given overall suture denier is as follows:

| Overall Suture Denier | Maximum Denier of Core |
|---|---|
| greater than about 125 to about 200 | 25-40 |
| greater than about 200 to about 300 | 40-60 |
| greater than about 300 to about 500 | 60-100 |
| greater than about 500 to about 800 | 125-200 |
| greater than about 800 to about 1200 | 200-300 |
| greater than about 1200 to about 2000 | 300-500 |
| greater than about 2000 to about 4000 | 500-1000. |

28. The suture of claim 26 wherein the maximum denier of the core for a given overall suture denier is as follows:

| Overall Suture Denier | Maximum Denier of Core |
|---|---|
| greater than about 125 to about 200 | 10-20 |
| greater than about 200 to about 300 | 20-30 |
| greater than about 300 to about 500 | 30-50 |
| greater than about 500 to about 800 | 75-120 |
| greater than about 800 to about 1200 | 120-180 |
| greater than about 1200 to about 2000 | 180-300 |
| greater than about 2000 to about 4000 | 300-600. |

29. The suture of claim 26 wherein the individual filaments are fabricated from a bio-absorbable polymer.

30. The suture of claim 26 wherein the individual filaments are fabricated from a polymer derived at least in part from one or more monomers selected from the group consisting of glycolic acid, glycolide, lactic acid and lactide.

31. The suture of claim 7 wherein for a given overall suture denier, the number of yarns and denier of individual filaments comprising a yarn of the spiroid braided suture are related to each other as follows:

| Overall Suture Denier | Number of Yarns | Denier of Individual Filaments |
|---|---|---|
| from about 50 to about 125 | from about 6 to about 12 | from about 0.8 to about 3.0 |
| greater than about 125 to about 200 | from about 6 to about 12 | from about 0.8 to about 3.0 |
| greater than about 200 to about 300 | from about 6 to about 12 | from about 0.8 to about 3.0 |
| greater than about 300 to about 500 | from about 9 to about 12 | from about 0.8 to about 3.0 |
| greater than about 500 to about 800 | from about 12 to about 15 | from about 0.8 to about 3.0 |
| greater than about 800 to about 1200 | from about 15 to about 20 | from about 0.8 to about 3.0 |
| greater than about 1200 to about 2000 | from about 15 to about 20 | from about 0.8 to about 3.0 |
| greater than about 2000 to about 4000 | from about 24 to about 34 | from about 0.8 to about 3.0. |

32. The suture of claim 7 wherein the water soluble, liquid polyhydroxy compound is glycerol.

33. The suture of claim 32 wherein the glycerol is admixed with calcium lactate.

34. The suture of claim 7 wherein the water soluble, liquid polyhydroxy compound is admixed with a non-aqueous thickener.

35. The suture of claim 7 wherein the water soluble, liquid polyhydroxy compound is admixed with a saturated aliphatic hydroxycarboxylic acid of the general formula $$R-\underset{H}{\overset{OH}{C}}-(CH_2)_n-COOR'$$

wherein R is hydrogen or methyl, R' is a metal selected from the group consisting of alkali metal and alkaline earth metal and n is 0 or 1, and hydrates thereof.

36. The suture of claim 35 wherein the water soluble, liquid polyhydroxy compound is admixed with calcium lactate.

37. The suture of claim 7 wherein the suture is surface-coated with a composition which enhances its lubricity and/or knot tie-down performance.

38. The suture of claim 7 wherein the composition is a bioabsorbable coating composition obtained by copolymerizing a polyether glycol with a mixture of lactide monomer and glycolide monomer or a preformed copolymer of lactide and glycolide.

39. The suture of claim 38 wherein the polyether glycol is selected from the group consisting of low molecular weight polyalkylene glycol and polyethylene oxide-polypropylene oxide copolymer.

40. The suture of claim 7 containing at least one medico-surgically useful substance.

41. The suture of claim 40 wherein the medico-surgically useful substance is a Human Growth Factor.

42. The suture of claim 7 filled with a filling composition comprising a surgical wound healing enhancing amount of at least one Human Growth Factor and as carrier thereof at least one water soluble, liquid polyhydroxy compound and/or ester thereof.

43. The suture of claim 42 wherein the carrier is glycerol.

44. The suture of claim 42 wherein the filling composition includes a thickener.

45. The suture of claim 44 wherein the thickener is a saturated aliphatic hydroxycarboxylic acid of the general formula $$R-\underset{H}{\overset{OH}{C}}-(CH_2)_n-COOR'$$

wherein R is hydrogen or methyl and R' is a metal selected from the group consisting of alkali metal and alkaline earth metal and n is 0 or 1, and hydrates thereof.

46. The suture of claim 45 wherein the thickener is calcium lactate.

47. The suture of claim 46 wherein the carrier is glycerol and the thickener is calcium lactate.

48. The suture of claim 44 wherein the carrier is glycerol and the thickener is calcium lactate.

49. The suture of claim 7 exhibiting reduced chatter and/or drag relative to a tubular braided suture of equivalent size.

50. The suture of claim 7 exhibiting increased knot security relative to a tubular braided suture of equivalent size.

51. A suture of solid spiroid braid construction coated with a composition which results in a reduced level of tissue drag of the suture compared with the tissue drag of a standard suture of the same overall denier, said suture being filled with a filling composition comprising a surgical wound healing enhancing amount of at least one Human Growth Factor and as carrier thereof at least one soluble, liquid polyhydroxy compound and/or ester thereof.

52. The suture of claim 51 wherein the carrier is glycerol.

53. The suture of claim 51 wherein the filling composition includes a thickener.

54. The suture of claim 53 wherein the thickener is a saturated aliphatic hydroxycarboxylic acid of the general formula

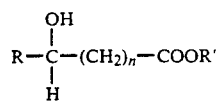

wherein R is hydrogen or methyl and R' is a metal selected from the group consisting of alkali metal and alkaline earth metal and n is 0 or 1 and hydrates thereof.

55. The suture of claim 54 wherein the thickener is calcium lactate.

56. The suture of claim 55 wherein the carrier is glycerol and the thickener is calcium lactate.

57. The suture of claim 53 wherein the carrier is glycerol and the thickener is calcium lactate.

* * * * *